US011040216B2

United States Patent
Degenaar et al.

(10) Patent No.: US 11,040,216 B2
(45) Date of Patent: Jun. 22, 2021

(54) IMPLANTABLE OPTRODE WITH A CONTROLLER CONFIGURED FOR OPERATION IN A STIMULATION MODE AND IN A DIAGNOSTIC MODE

(71) Applicant: UNIVERSITY OF NEWCASTLE UPON TYNE, Newcastle upon Tyne (GB)

(72) Inventors: Patrick Degenaar, Newcastle upon Tyne (GB); Hubin Zhao, Newcastle upon Tyne (GB)

(73) Assignee: University of Newcastle Upon Tyne, Newcastle upon Tyne (GB)

( * ) Notice: Subject to any disclaimer, the term of this patent is extended or adjusted under 35 U.S.C. 154(b) by 733 days.

(21) Appl. No.: 15/319,721

(22) PCT Filed: Jun. 18, 2015

(86) PCT No.: PCT/GB2015/051787
§ 371 (c)(1),
(2) Date: Dec. 16, 2016

(87) PCT Pub. No.: WO2015/193674
PCT Pub. Date: Dec. 23, 2015

(65) Prior Publication Data
US 2017/0143985 A1 May 25, 2017

(30) Foreign Application Priority Data
Jun. 18, 2014 (GB) ..................... 1410886

(51) Int. Cl.
*A61N 5/06* (2006.01)
*A61B 17/00* (2006.01)
*A61B 18/00* (2006.01)

(52) U.S. Cl.
CPC ......... *A61N 5/0601* (2013.01); *A61N 5/0622* (2013.01); *A61B 2017/00084* (2013.01);
(Continued)

(58) Field of Classification Search
CPC ............... A61N 5/0601; A61N 5/0622; A61N 2005/0612; A61N 2005/0626; A61N 2005/0651
(Continued)

(56) References Cited

U.S. PATENT DOCUMENTS

| 5,259,380 A | 11/1993 | Mendes et al. |
| 2005/0085875 A1* | 4/2005 | Van Zuylen ......... A61N 5/0616 607/88 |

(Continued)

FOREIGN PATENT DOCUMENTS

| WO | 2012/048891 A1 | 4/2012 |
| WO | 2012048891 A1 | 4/2012 |

OTHER PUBLICATIONS

International Search Report and Written Opinion of the International Searching Authority, dated Oct. 2, 2015, for International Application No. PCT/GB2015/051787, 15 pages.
(Continued)

*Primary Examiner* — Aaron F Roane
(74) *Attorney, Agent, or Firm* — Seed IP Law Group LLP

(57) ABSTRACT

An optrode arrangement for delivering optical stimulation to target tissue in a patient, the optrode arrangement comprising an implantable optrode comprising at least one electrically powered light emitter and an electrical circuit and control lines for controlling the light emitter, whereby an associated controller has two modes of operation: a stimulation mode in which it is configured to control the light emitter to deliver optical stimulation to the target tissue and
(Continued)

a diagnostic mode in which it is configured to determine a condition of the light emitter and/or the optrode.

20 Claims, 14 Drawing Sheets

(52) U.S. Cl.
CPC ............... *A61B 2018/00898* (2013.01); *A61N 2005/0612* (2013.01); *A61N 2005/0626* (2013.01); *A61N 2005/0651* (2013.01)

(58) Field of Classification Search
USPC ........................................................... 607/88
See application file for complete search history.

(56) References Cited

U.S. PATENT DOCUMENTS

| | | |
|---|---|---|
| 2006/0142823 A1 | 6/2006 | Whang |
| 2011/0125077 A1 | 5/2011 | Denison et al. |
| 2012/0197357 A1* | 8/2012 | Dewey ................. A61B 18/203 607/89 |
| 2013/0046148 A1 | 2/2013 | Tathireddy et al. |
| 2013/0317572 A1 | 11/2013 | Zhu et al. |
| 2013/0317573 A1* | 11/2013 | Zhu ...................... A61N 5/0622 607/89 |
| 2014/0128941 A1 | 5/2014 | Williams |

OTHER PUBLICATIONS

Search report of the Intellectual Property Office of the United Kingdom, dated Feb. 5, 2015, for British Application No. GB1410886. 4, 3 pages.

* cited by examiner

Vout vs normal/broken optrode

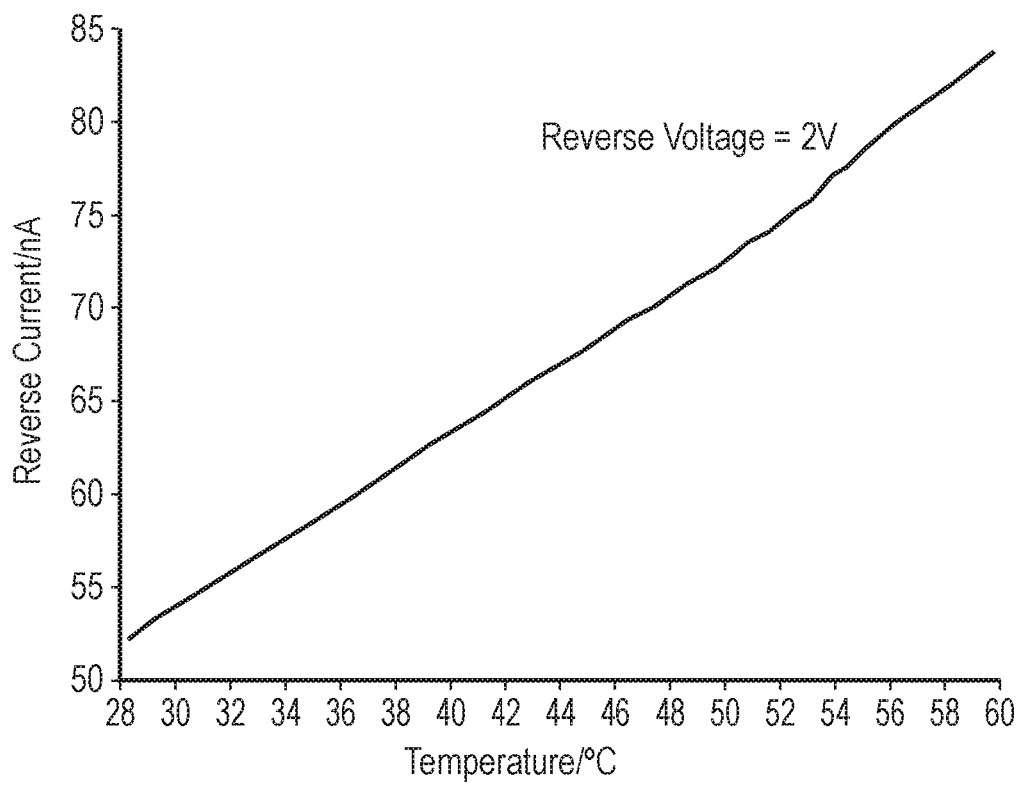
FIG. 14 Reverse Current vs Temperature
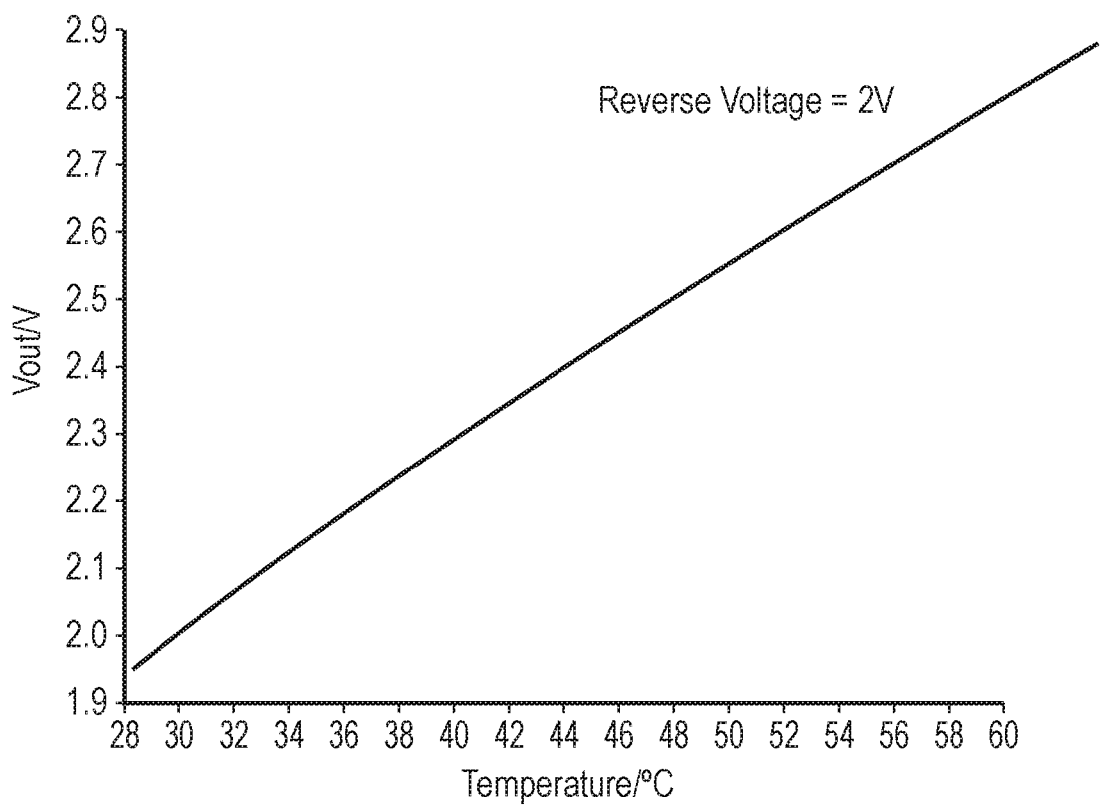
FIG. 15 Vout vs Temperature

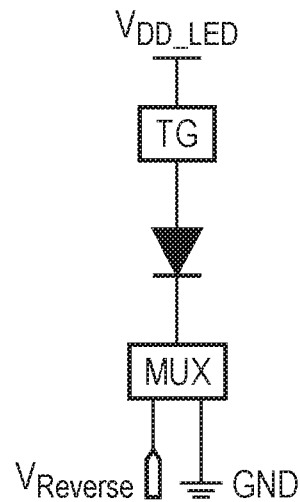
FIG. 16 Reverse Control Circuit
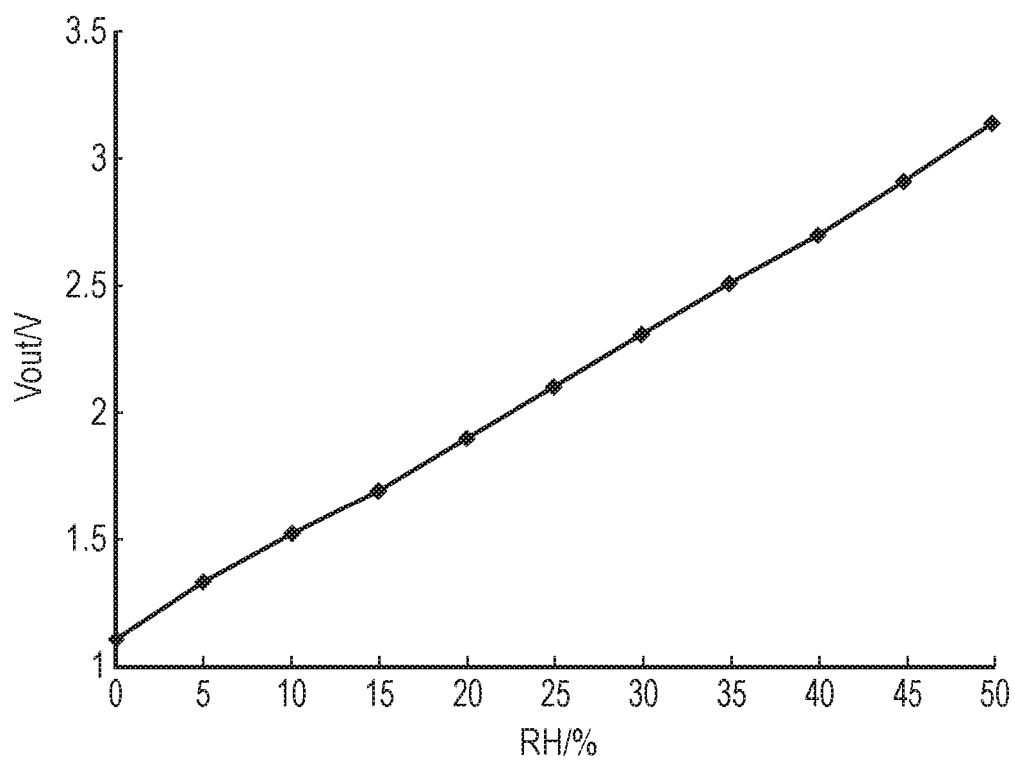
FIG. 17 Vout vs Humidity

IMPLANTABLE OPTRODE WITH A CONTROLLER CONFIGURED FOR OPERATION IN A STIMULATION MODE AND IN A DIAGNOSTIC MODE

FIELD OF THE INVENTION

The invention relates to implantable optrode arrangements and methods of controlling them.

BACKGROUND

Neural stimulation for central and peripheral nervous systems has been widely utilized in neural prostheses and therapies area. Typical applications include retinal and cortical visual prostheses, bladder prostheses, upper and lower limb prostheses for spinal cord injury and stroke, cochlear and brain-stem auditory prostheses, cortical recording for cognitive control of assistive devices, vagus nerve stimulation for epilepsy and depression and deep brain stimulation (DBS) for essential tremor, Parkinson's disease, epilepsy, dystonia, and depression [1].

Existing electrode-based deep brain stimulation methods indiscriminately stimulate all neurons within a given volume, including cells that are not implicated for the disease state, leading to unwanted side effects or even reduced efficacy as opposing, excitatory, and inhibitory cell types are affected by the electrodes. The precision of implanted electrodes is limited to the size of the electrode which in turn is limited by degradation of the electrode materials. Typically for brain pacemakers and other neuromodulators, this is of the order of one millimeter. A key limitation is that the stimulating electric field is not specific to any particular cell type of sub-circuit. This means that parts of the target area are not under perfect control.

With the discovery of the channelrhodopsin-2(ChR2) in 2003 [2], a new optical interface with nerve cells was created. ChR2 is a light-sensitive cation channel and mostly used in optogenetics. Together with advanced variants and chloride pumps which can inhibit neural activity, it gave rise to the new field of 'Optogenetics'. This is based on genetic photosensitization of neurons which can then be optically excited and inhibited. The key caveat is that the light requirement is very high, necessitating ultra high radiance light emitting diodes or lasers. As stimulus wavelengths are in blue end of the visible spectrum, such light is readily scattered in neural tissue. Thus implantable structures ('optrodes') are required to deliver light deep into the neural tissue.

In recent years, the fields of electrophysiology and prosthetics have been revolutionized by optogenetic neural stimulation techniques [3-5]. As the sensitizing proteins can be genetically engineered into specific kinds of neurons, this technique can be used to explore complex brain circuits and neurological and psychiatric illnesses such as blindness, spinal cord injuries, Parkinson's disease and epilepsy [6-8]

WO 2012/134704 describes an example of a system for optogenetic modulation of cells within a patient. This document describes a system in which a viral vector including a genetic agent encoding for one of more light sensitive proteins is delivered to a treatment site within a patient. A sensor is used to sense a bioelectrical signal related to a neurological condition of the patient and an optical stimulator is configured to deliver light to cells transduced with the viral vector based on the bioelectrical signal sensed by the sensor. The optical stimulator delivers optical stimulation to the patient via implantable optical fibers that are connected to a light source that is remote from the site of the treatment site. In another example, this document describes the use of a light source, such as a light emitting diode (LED) implanted at the treatment site. An electrically conducting lead is implanted to extend from an optical stimulation controller to the LED to conduct electrical energy to power the LED.

SUMMARY OF INVENTION

One of the important challenges in optogenetic neural stimulation is the development of devices ('optrodes') to deliver light to target areas of brain tissue. The requirements include battery operation (low power), small implant size (miniaturization), safety (biocompatibility) and reliability (stable operation).

In particular, in order to create the desired therapeutic interventions, optrodes will need to be created which deliver the required ultra-high intensity light. A key benefit in intervention is gained through the use of electronic recording methodologies, the combination of which allows for closed loop neuromodulation. Building intelligence and light sources into such optrodes then poses challenges. If implanted in the brain, it is undesirable to replace them unless absolutely necessary due to damage to sensitive neural tissue. As such building in diagnostic sensors to ensure safe use provides significant advantage. Such optrodes also ideally have intelligence to provide stimulation of multiple sites and recording mechanisms to interpret subsequent neural signalling.

The present inventors have recognised that by using light sources implanted at the treatment site, the need for relatively bulky (relative to power leads) optical fiber bundles can be avoided. Moreover, in fiber based systems the delivery of light to the treatment site is very dependent on the coupling efficiency of light source to fibers. It can also be challenging to achieve large numbers of individually addressable stimuli points in a compact system with this approach. Consequently, approaches using individually addressable implanted light sources can have lower overall power requirements and provide highly compact implementations.

For human intervention, safety and reliability are particularly important considerations in the design of optrodes. Whereas implantable optic fibres and waveguides may mechanically break on insertion, their passive nature prevents subsequent damage through heating, malfunction or electrical discharge. In contrast implantable light emitters such as Light Emitting Diodes need to be electrically driven and inefficiencies in light production will result in local heating. There is therefore a danger that local hotspots can damage the surrounding neural tissue. With long term electric fields in implanted devices there is a chance for slow degradation which can make a device unreliable over the years to decades of implant lifetime. Finally, mechanical failure on insertion brings the risk of electrical discharge into the tissue of the control wires to the light emitters are exposed.

A general aim of the present invention is to provide an implantable optical stimulator (optrode) that positions light sources, for example LEDs, at a treatment site in a patient, for which safe and reliable operation can be ensured once the optrode is implanted. What is proposed, in general terms, is a diagnostic function to monitor a condition of the optrode, for example so that the condition of the optrode can be checked after implantation but before the optrode is operated in a stimulation mode. This approach improves the reliability and safety of the optrode for implantable applications.

In a first aspect the invention provides an optrode arrangement for delivering optical stimulation to target tissue in a patient, the optrode arrangement comprising:
- an implantable optrode comprising at least one electrically powered light emitter; and
- an electrical circuit and control lines for controlling the light emitter;
- wherein the controller has two modes of operation, a stimulation mode in which it controls the light emitter to deliver optical stimulation to the target tissue and a diagnostic mode in which it determines a condition of the light emitter and/or the optrode.

In some embodiments, determining a condition of the optrode comprises determining the condition of one or more light emitters on the optrode and using the condition of the light emitter(s) to determine the condition of the optrode.

Light emissive devices have a threshold forward voltage before light is emitted. Thus, in the stimulation mode, a voltage above a threshold voltage is applied to an input of the light emitter to cause it to emit light for optical stimulation. It is most convenient to utilise these diodes themselves as key sensors. In some cases such as temperature measurement, measurement may be taken during operation. Alternatively in purely diagnostic mode, any voltage (forward or reverse) applied to the input of the light emitter does not exceed said forward threshold voltage, so no undesired optical stimulation takes place.

In some embodiments the controller is configured to determine the condition of the light emitter and/or the optrode itself to be normal or abnormal. The controller may be configured to generate an alert in the case that it is determined that the condition of the light emitter or the optrode is abnormal. Additionally or alternatively, the controller may be configured to prevent subsequent operation in the stimulation mode when it is determined that the condition of the light emitter is abnormal. In some embodiments the optrode comprises multiple light emitters and the condition of each light emitter is individually determined. In such embodiments subsequent operation of abnormal light emitters can be subsequently prevented whilst normal operation of other light emitters continues. Similarly, if it is determined that a portion of the optrode is damaged (for example based on the condition of light emitters along the length of the optrode) then operation of the damaged portion of the optrode can be prevented whilst operation of the remainder of the optrode continues.

In some embodiments, in the diagnostic mode of operation, the controller determines a condition of the light emitter based on at least a voltage drop across the light emitter. The controller may, for example, comprise a diagnostic circuit configured to output a measure of voltage drop across the light emitter. In some embodiments the controller is configured to compare the output of the diagnostic circuit with an expected output for a normal condition of the light emitter and to determine that the light emitter has an abnormal condition when the output of the diagnostic circuit is different from the expected output.

In some embodiments, the optrode arrangement may comprise a thermal sensor for measuring a temperature of the optrode, wherein in the diagnostic mode of operation, the controller determines a condition of the light emitter based on at least an output from the thermal sensor. In some embodiments, the light emitter's (e.g. LEDs) may themselves be used as the thermal sensors. In particular, in the case of a light emitter (e.g. and LED) in which the current flowing through the light emitter varies with temperature for a given potential across the light emitter, a measure of the current flowing can be used to determine the temperature of the light emitter. The temperature of the surrounding tissue can be inferred from the light emitter temperature if desired, for example so that operation of the light emitter can be ceased if the inferred surrounding temperature exceeds a predetermined threshold.

In some embodiments, the optrode arrangement may comprise a humidity sensor for providing a measure of the degradation of the optrode, wherein in the diagnostic mode of operation, the controller determines a condition of the light emitter based on at least an output from the humidity sensor.

In some embodiments, the optrode arrangement may comprise a plurality of stimulation sites space apart along the optrode from one another, each stimulation site comprising at least one light emitter. One or more of the light emitters may be used in the stimulation mode to more precisely control the location of the applied optical stimulation.

Where there are multiple stimulation sites on the optrode, each stimulation site may comprise one, two, three or more light emitters. Where there are multiple light emitters at a stimulation site they may be used together to increase the intensity of optical stimulation. Alternatively, one light emitter may be designated a main emitter, with one or more other emitters being used as backups in the event that the main emitter ceases to function correctly.

Embodiments may use any suitable light emitters. Suitable light emitters include light emitting diodes. Other suitable light emitters include Vertical Cavity Surface emitting lasers, Bragg lasers and other lasing structures. In such embodiments, the wavelength may be determined by bandgap engineering of the structure or by secondary emission via wavelength shifting components such as quantum dots, fluorescent and phosphorescent materials. In addition, some embodiments may also include micro-optical components for example to collimate the light or otherwise improve optical efficiency.

In embodiments the target tissue will typically be nerve cells. However, optogenetics is at its core the optical stimulation of ion flows in an out of cells. Thus further application could be achieved in other 200 non-neural cells in the body. This could include indirect stimulation of the nervous system via astrocytes or cells of the endocrine system. It could also stimulate cells of the endocrine and lymphatic system for non-neuronal purposes such as hormone imbalances. There may also be applications in epithelial, muscle (e.g. cardiac), Hepatic, pancreatic, renal, digestive and urinary systems.

In a second aspect, the invention provides a method of controlling an optrode arrangement, the optrode arrangement being for delivering optical stimulation to target tissue in a patient and comprising an implantable optrode having at least one electrically powered light emitter, the method comprising, prior to optical stimulation of the tissue, operating the optrode arrangement in a diagnostic mode to determine a condition of the light emitter and/or the optrode itself.

In the diagnostic mode the optrode does not optically stimulate the target tissue.

In a third aspect, the invention provides a method of delivering optical stimulation to target tissue in a patient using at least one electrically powered light emitter on an implanted optrode, the method comprising checking the condition of the light emitter and/or the optrode integrity. In some embodiments, where failure (or abnormal operation/ condition) is determined, only the functional sections of the optrode will be activated in stimulation mode or in some cases (e.g. where the damage is extreme) the whole optrode will remain or become deactivated.

In a fourth aspect the invention provides a method of implanting an optrode in a patient, the optrode comprising at least one electrically powered light emitter for delivering optical stimulation to tissue adjacent the implanted optrode, the method comprising implanting the optrode and, following implantation, determining a condition of the optrode prior to the optrode being used for optical stimulation.

Some advantages of embodiments of the optrode technology proposed here are the potential for cell specificity, high temporal and spatial resolution in the micrometer range, which has potential for the stimulation of brain substructures, possible using implanted light emitters, whilst incorporating appropriate control, by way of the diagnostic mode, to mitigate the risks noted above associated with damage to the optrode during implantation.

BRIEF DESCRIPTION OF THE FIGURES

An embodiment of the invention is described below by way of example with reference to the accompanying figures, in which:

FIGS. 14 and 15 show graphs of temperature versus reverse current and Vout respectively for operation of an LED used in the optrode;

FIG. 16 shows a reverse control circuit for the optrode LEDs;

FIG. 17 shows a graph of $V_{out}$ versus humidity;

DESCRIPTION OF EMBODIMENT

An example of an implantable electrode arrangement is described below to help illustrate the concepts disclosed herein. The optrode arrangement is intended to be used as the light stimulation element of an optogenetics system. In particular it is proposed that the optrode be implanted at a treatment site in a patient (usually a human). Once implanted in vivo, it can be difficult to check the integrity of the optrode. However, it can be important to do so because optrodes tend to be fragile and may be damaged during the implantation procedure. If there is damage to the optrode, there is a risk that power leads for light sources on the optrode will discharge current into tissue around the optrode if it is operated in a stimulation mode, potentially causing serious damage.

As it is may be difficult to assess the integrity of the implant from x-Ray/CT scans, the present inventors propose incorporating circuitry to assess continued functionality. This can allow for disabling of non-functional stimulation, which not only saves energy, but can prevent undesirable current discharge into the tissue in the event of probe rupture.

The main circuits of the exemplary optrode arrangement proposed now consist of a communication system, LED control and probe sensing system. The former uses an adapted SPI protocol. The LED control as will be described consists of individually addressable cells with individual memory units to allow pulse width light modulation. The system incorporates a method to perform a (LED) subthreshold voltage scan across the LED to determine its continued usable state. This can allow the user or diagnostic technician to determine whether there has been component failure and whether or not to switch to an alternate LED. This proposed sensing methodology significantly enhances the safety and stability of the optrode.

More specifically, optrodes in accordance with some embodiments of the present invention are operable in a diagnostic mode that can detect an abnormal condition in the optrode, for example in one or more of the LEDs, using current that are lower than those required for stimulation at that are therefore much less likely to cause any tissue damage if the integrity of the optrode is compromised.

Figure 1:
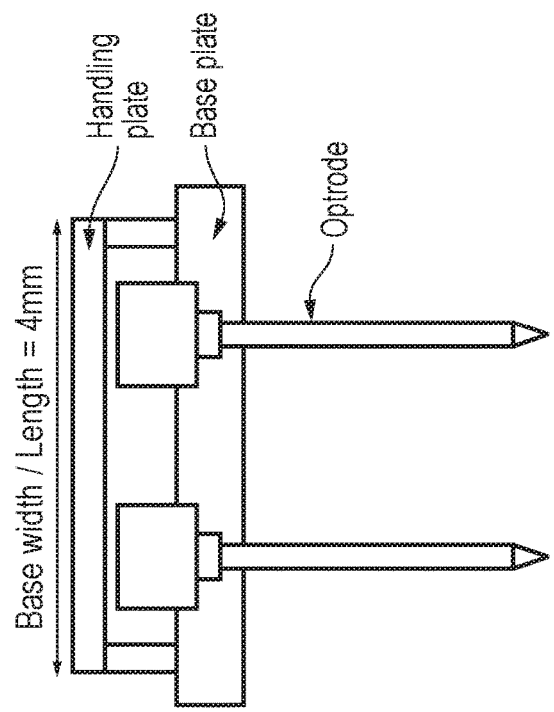
FIG. 1 is a schematic illustration of an optrode-based neural stimulation arrangement in accordance with an embodiment of the present invention.
Figure 3:
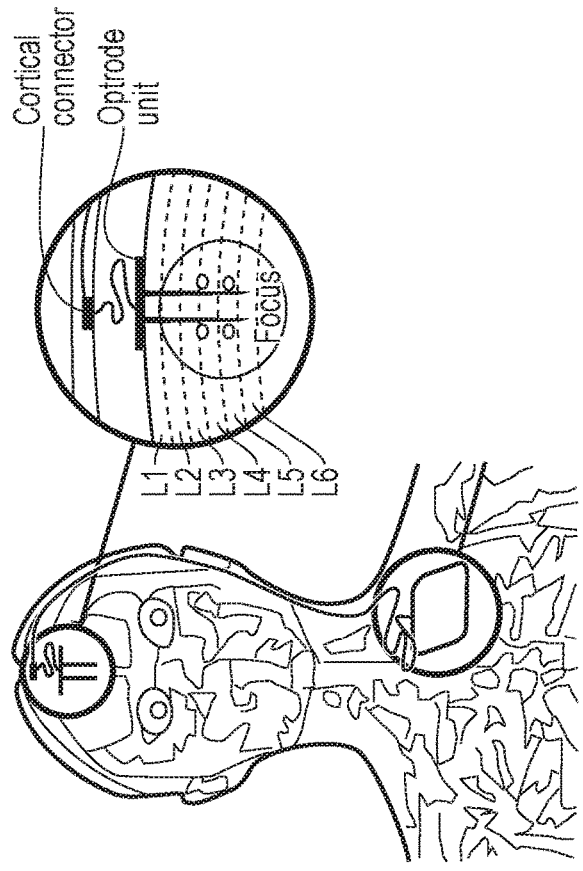
FIG. 3 is a schematic illustration of the structural configuration of the neural stimulation arrangement of FIG. 1.
Figure 2:
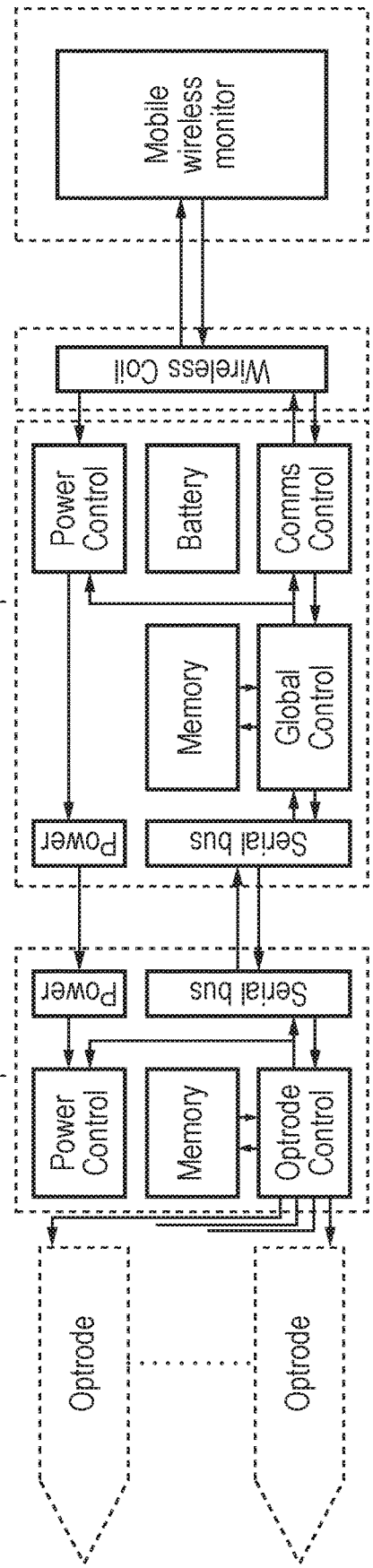
FIG. 2 is a schematic illustration of the system architecture of the neural stimulation arrangement of FIG. 1.

With reference to FIGS. 1 to 3, two possible arrangements are envisaged for the optrode. In the first, key control electronics are incorporated into the optrode itself. In the second control electronics are incorporated into a mechanical plate holding the optrode in place. It is also possible to have electronic control circuits on both. The integrated optrode arrangement includes communication circuitry in the head and control circuitry in the head and/or shaft of the optrode.

Optrodes can be used individually or in a cluster arrangement of two or more optrodes. For the latter, a mechanical plate may be used to stabilise the multiple optrodes, as shown in FIG. 3.

Thus, as shown for example in FIGS. 2 and 3, an optical stimulation arrangement may include two optrodes mounted on a baseplate. As explained in more detail below, each optrode includes multiple light emitters (in this example LEDs) spaced along the length of the optrode shaft. Drive circuitry for the light emitters is contained in the optrode head, as explained further below with reference to FIG. 4. Optrode control and power control circuitry for both optrodes is housed in the baseplate, which is then connected to a subcutaneous implant unit, physically spaced from the baseplate and connected by a cable. The subcutaneous unit includes a global controller, further power control components and a communication controller. The subcutaneous unit provides power and control signals to the baseplate, which in turn provides power and control signals to the optrodes. In a stimulation system, although not shown here, the subcutaneous implant unit may be connected to multiple baseplates, each of which can support one or more optrodes. Communication with the subcutaneous implant unit is achieved wirelessly in this example (and the unit includes a wireless coil to facilitate this), allowing monitoring and control of the system wirelessly from a remote monitor unit, for example a mobile (e.g. handheld) wireless monitor that could be used by a patient or a physician for example.

The particular example used here is a CMOS-based optrode for neural stimulation with optogenetic methodology. The optrode is configured to provide six stimulation sites spaced from one another along the optrode. The stimulation sites may be spaced at 4 mm intervals to match the cortical layers of the brain. Other embodiments may have more of fewer stimulation sites and/or use different spacing.

In this example, each stimulation site comprises three micro light emitting diodes (LEDs) to achieve local light delivery for neural stimulation. In other examples, each site may have one, two or more than three LEDs. The stimulation sites may each have the same number of LEDs as one another or one or more sites may have a different number of LEDs to one or more other sites.

To achieve this particular optrode design, the present inventors have designed and fabricated a CMOS wafer within which the optrode forms part. The optrode can then be cut out using laser cutting and combined with Gallium Nitride μLEDs.

Figure 4:
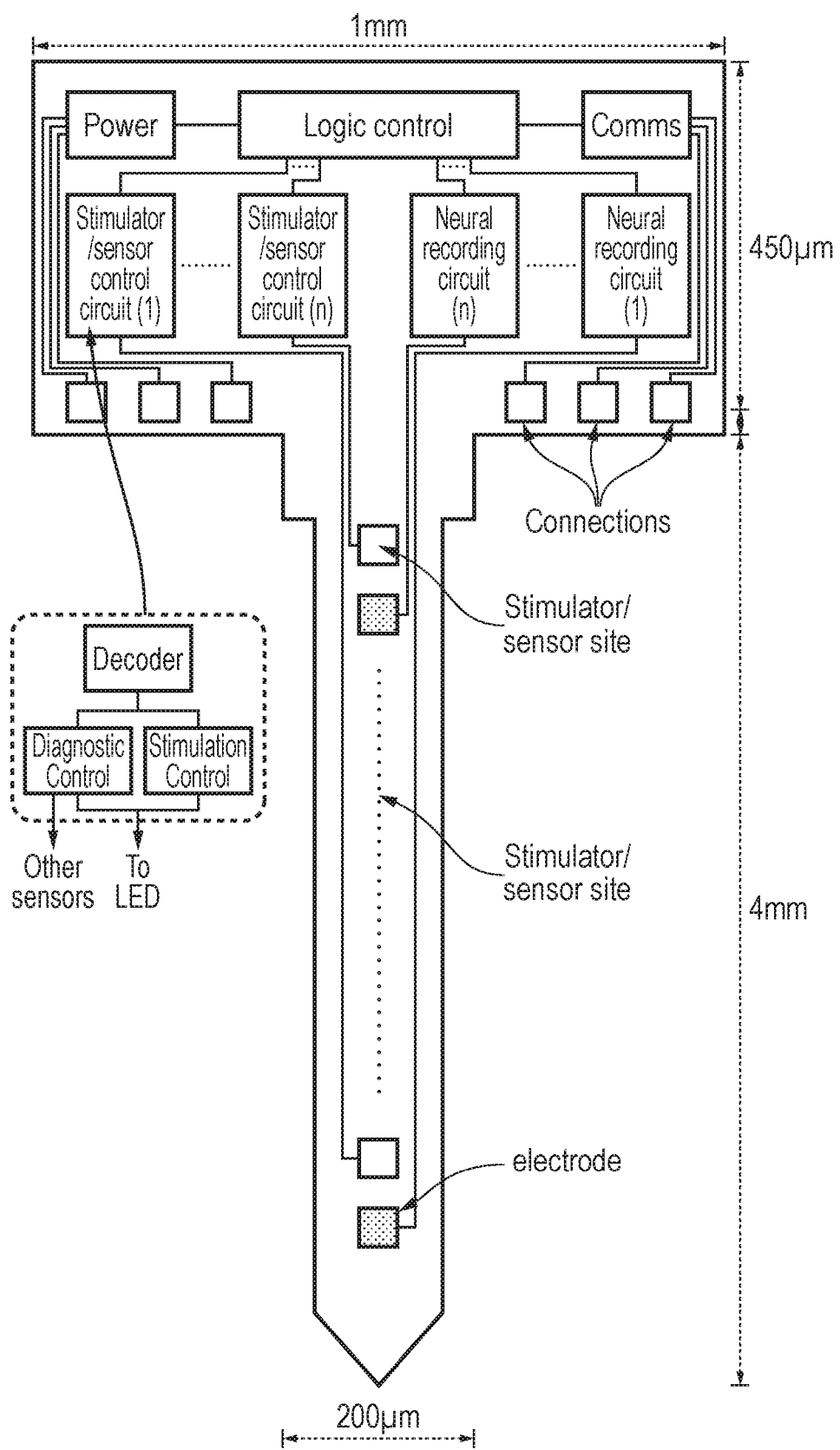
FIG. 4 is a schematic illustration of the system architecture of one optrode of the neural stimulation arrangement of FIG. 1.

As seen in FIG. 4, the proposed optrode includes two parts: a head part which comprises circuits (in this example CMOS circuits) to drive the LEDs and a shaft part (again, in this example, of CMOS construction). The stimulation sites are evenly spaced at intervals along the shaft. This enables variation/selection of the stimulation depth using a selected one or more of the LEDs, providing high spatial resolution. In the example shown in FIG. 4, the optrode shaft also includes a corresponding number of sensor sites, one adjacent each stimulator site, for sensing electrical signals from tissue (e.g. neural signalling) in order to allow for closed loop neuromodulation.

As noted above, each stimulation site has an LED cluster that includes three LEDs in each LED cluster. In some implementations, one LED can be used as a main LED and the other two be intended as backup LEDs to be used, for example, if the main LED is or becomes defective. This approach enhances the robustness and durability of the stimulation sites.

Eighteen bond pads are formed on the shaft part of the optrode for LED connections. Six I/O pads are formed at the bottom of the optrode head for external input/output. Additionally, Electrostatic Discharge (ESD) protection may be employed to improve system reliability.

In this example, the head part of the optrode includes a control block for each LED, so that each LED may be separately controlled to be on or off. Thus, in the case where there are six stimulation sites, each with three LEDs, the head part includes 18 LED control blocks. The head part of the optrode also includes a global logic control block to provide global addressing and control of the LED control blocks.

In accordance with the concept disclosed herein, each LED control block has two operating modes: a stimulation mode; and a diagnostic mode. In the diagnostic mode an abnormal condition of the optrode LEDs can be detected.

The control unit of the optrode arrangement is in turn controlled by a master controller. As with most brain pacemaker units a battery and processing unit is implanted in the chest where it can be upgraded easily. There is then a lead to control the brain implant. The master controller can perform a scan post-implant to determine any mechanical damage post implantation. It can also direct long term diagnostics on the humidity (water penetration into the device) and temperature profile during operation.

Light stimulation is achieved my irradiating a quantity of photons to the target tissue within a short period of time (typically 1-100 ms). This quantity is determined by the light intensity and pulse duration. It is therefore possible to interleave diagnostic measurement between light emission pulses. In the case of temperature, this could be measured concurrently with optical emission. Where a threshold is exceeded a warning signal could be sent to the control system to turn the LED off.

Such diagnostic scanning could be performed as one or both of an automated process within the control system and external user command. In the former case (or the latter case), upon detection of an abnormal condition, a warning signal can be passed back to the user or operator.

The optrode arrangement includes one or more sensors or circuits that are used in the diagnostic mode to detect the presence of an abnormal condition. More specifically, in the present example, a diagnostic circuit is used (described in more detail below) to measure a voltage drop over the LED when a series of test voltages are applied to an LED input. This is effectively an output voltage-current scan. Online/real-time recording (e.g. during operation) would only be able to determine a single voltage which can be compared to history and to previous full diagnostic scans.

In other examples, further sensors may be used as an alternative or in addition to measuring the voltage drop across the LED. For example, thermal sensors that monitor the surface temperature of the optrode can be used in conjunction with a control mechanism to prevent the LEDs from overheating tissue. In some examples, the LED itself may be used to infer temperature of the surrounding tissue. More specifically, the junction temperature in the LED can be calculated from the current flowing through the LED when reverse biased with a given bias potential (the current flow is temperature dependent) and the surrounding tissue temperature can be inferred (e.g. empirically) from the calculated junction temperature.

Another exemplary sensor is a humidity sensor to determine degradation of the hermeticity of the device. The humidity sensor may, for example, take the form of a sensor with a sacrificial layer to monitor slow degradation, thus providing a real time prediction of device lifetime. The sensor output may be used to activate a cut-off circuit to turn off the optrode arrangement should it become so degraded that its performance is no longer deterministic.

Especially where multiple sensors/circuits are used in the diagnostic mode the outputs from all sensors/circuits may be provide to a control system that uses the outputs in combination to determine the state of the optrode arrangement.

The diagnostic mode may be run after implantation of the optrode, before the optrode arrangement is first used for stimulation. This can reliably detect damage to the optrode incurred during the implantation procedure. If damage is detected, a damaged part of the optrode can be isolated and only properly functions parts of the optrode used for stimulation. If the damage is sufficiently bad then the complete optrode or cluster of optrodes may be isolated and not used or the optrode can be removed before any damage is done to the patient.

Figure 5:
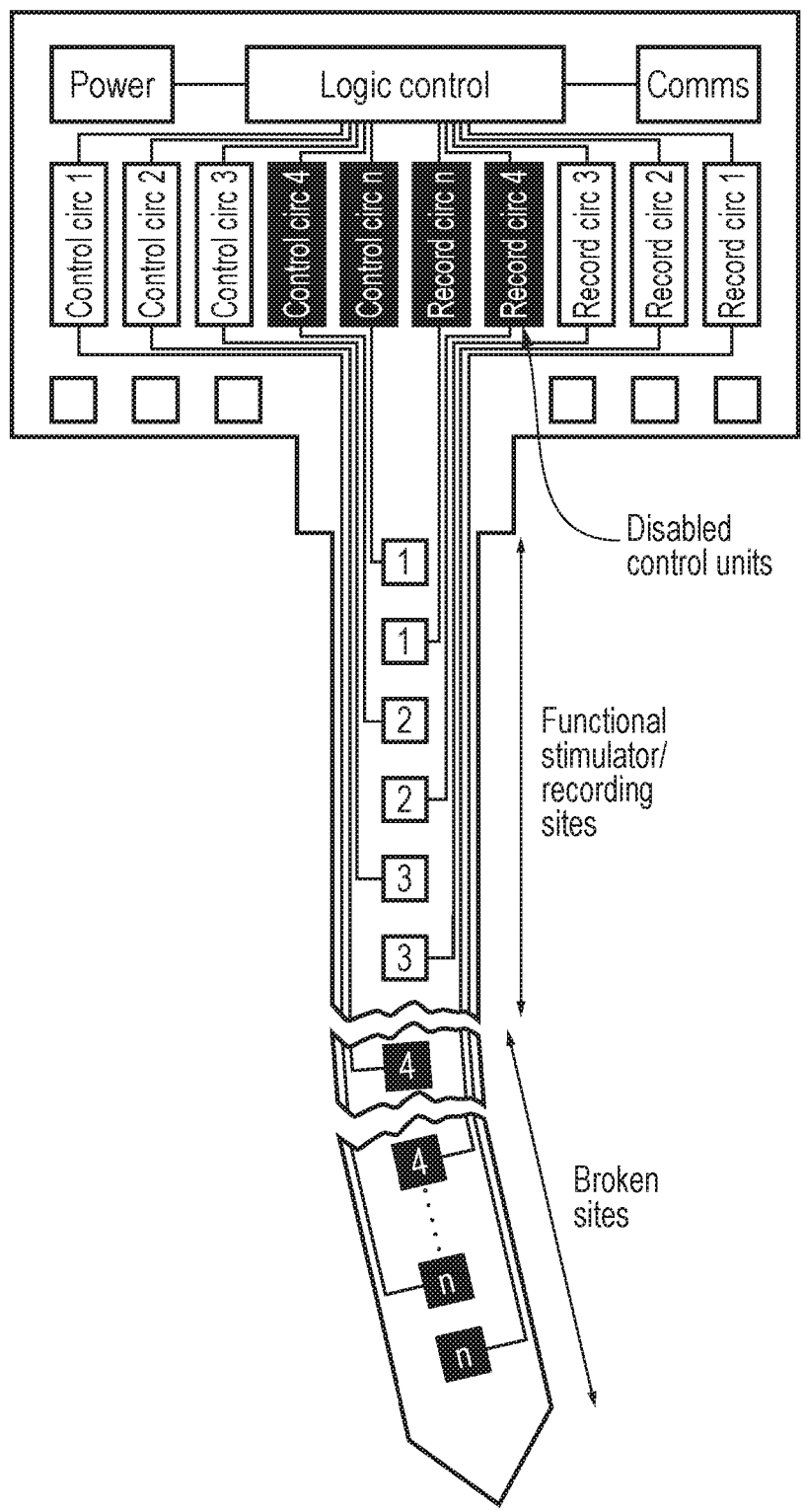
FIG. 5 is a schematic of the system architecture of one optrode (similar to FIG. 4), illustrating the case where the optrode is damaged.

For example, as shown in FIG. 5, where there is damage towards the tip of an optrode, as the stimulation sites are individually controlled, stimulation sites below the damaged region can be disabled, whereas stimulation sites above the damaged region can be operated as normal.

In some implementations, the diagnostic mode is run periodically to check the condition of the optrode. It may for example be run yearly, monthly, weekly, daily or more regularly. Alternatively it may be run on demand, for example during a patient consultation with a physician or technician.

In some implementations, the optrode arrangement may switch quickly between stimulation and diagnostic modes so that the condition of the optrode is monitored during optical stimulation of the tissue. This switching may for example be within the range of microseconds to milliseconds. i.e. it can either be a high speed interleaving or more simply a post stimulus recording. The former is more accurate, the latter is more convenient. This may be beneficial, for example, when using a temperature sensor to ensure there is no overheating of the tissue by the LEDs.

In one exemplary mode of operation currently envisaged a breakage sensor (i.e. to determine damage to the optrode or the LEDs) would be used once—after insertion and before powering up the device for stimulation operation; the humidity sensors would be operated periodically (but infrequently, e.g. yearly, monthly, weekly or daily) to see whether there was any change in the long term performance of the device and thermal sensing would be on a calibration basis, but also could be closed loop—so that LEDs would automatically turn off if they exceed a certain safe threshold temperature.

Figure 6A:
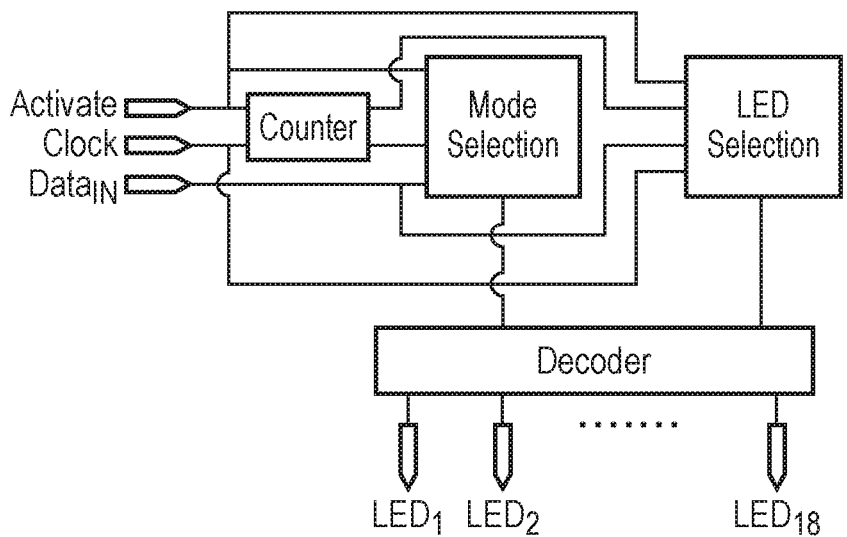
FIG. 6a is a simple block diagram of a logic control circuit for the optrode of FIG. 4
Figure 7A:
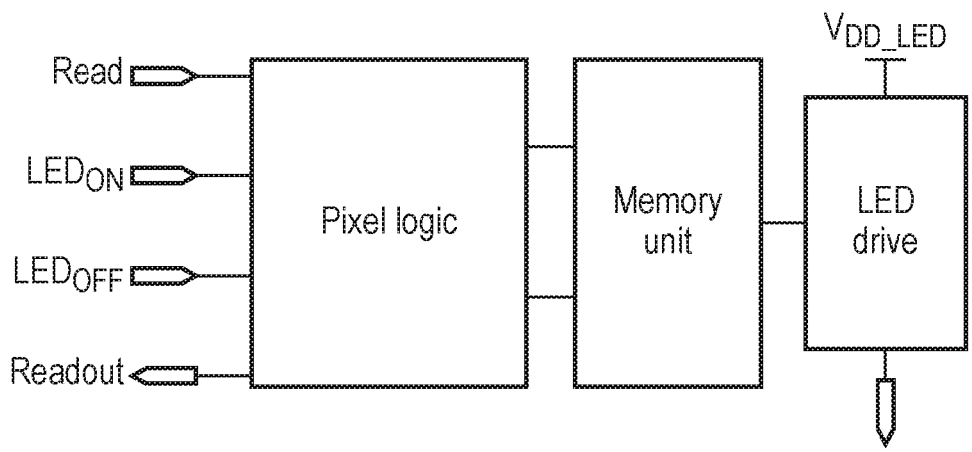
FIG. 7a is a simple block diagram of a simulation control circuit for the optrode of FIG. 4
Figure 8A:
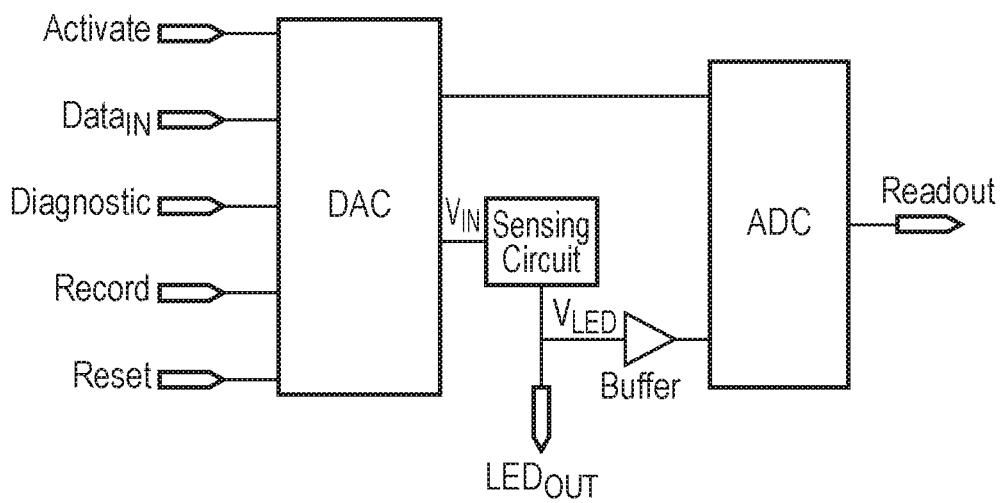
FIG. 8a is a simple block diagram of a diagnostic circuit for the optrode of FIG. 4
Figure 6B:
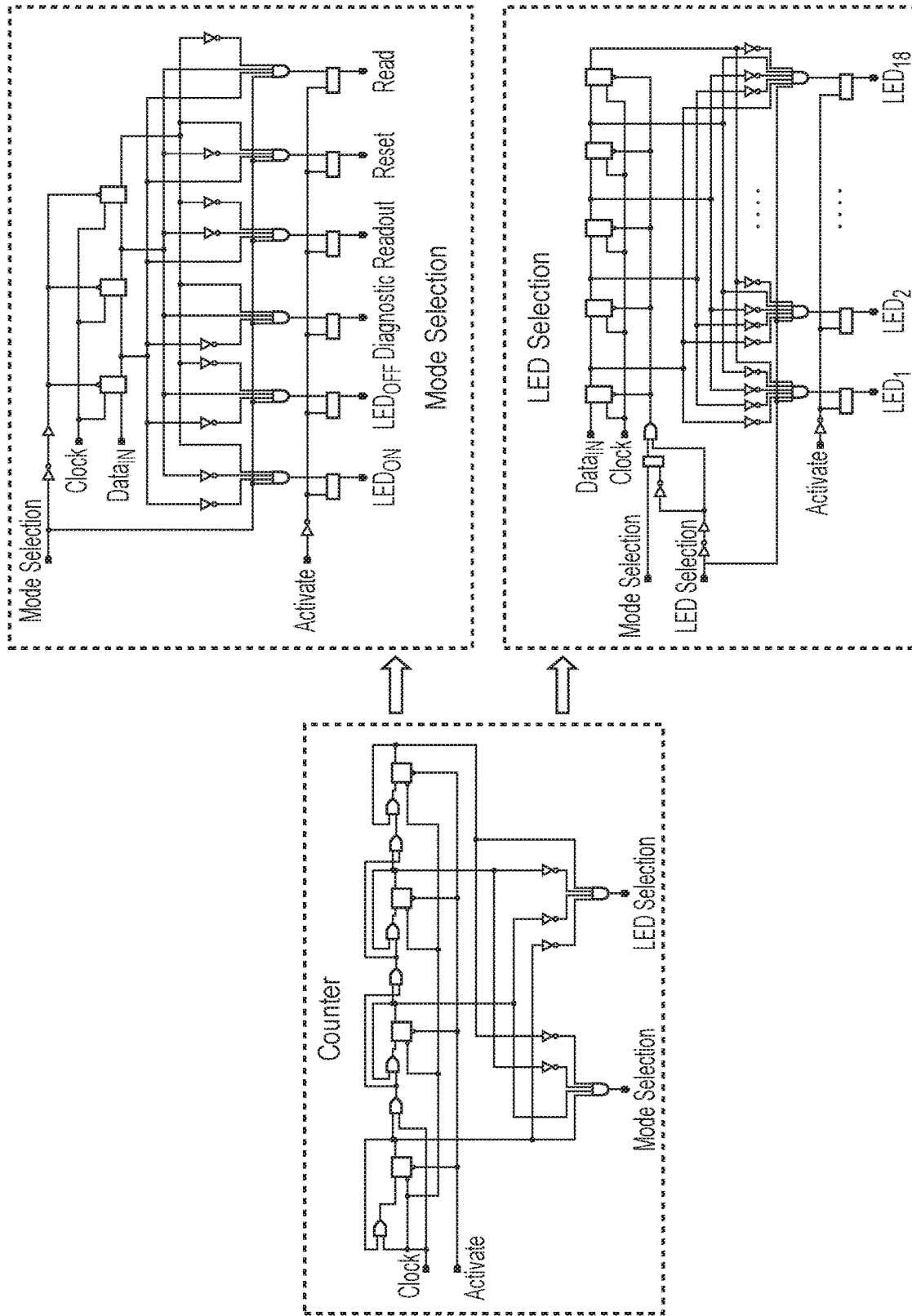
FIG. 6b is a more detailed diagram of the circuit.
Figure 7B:
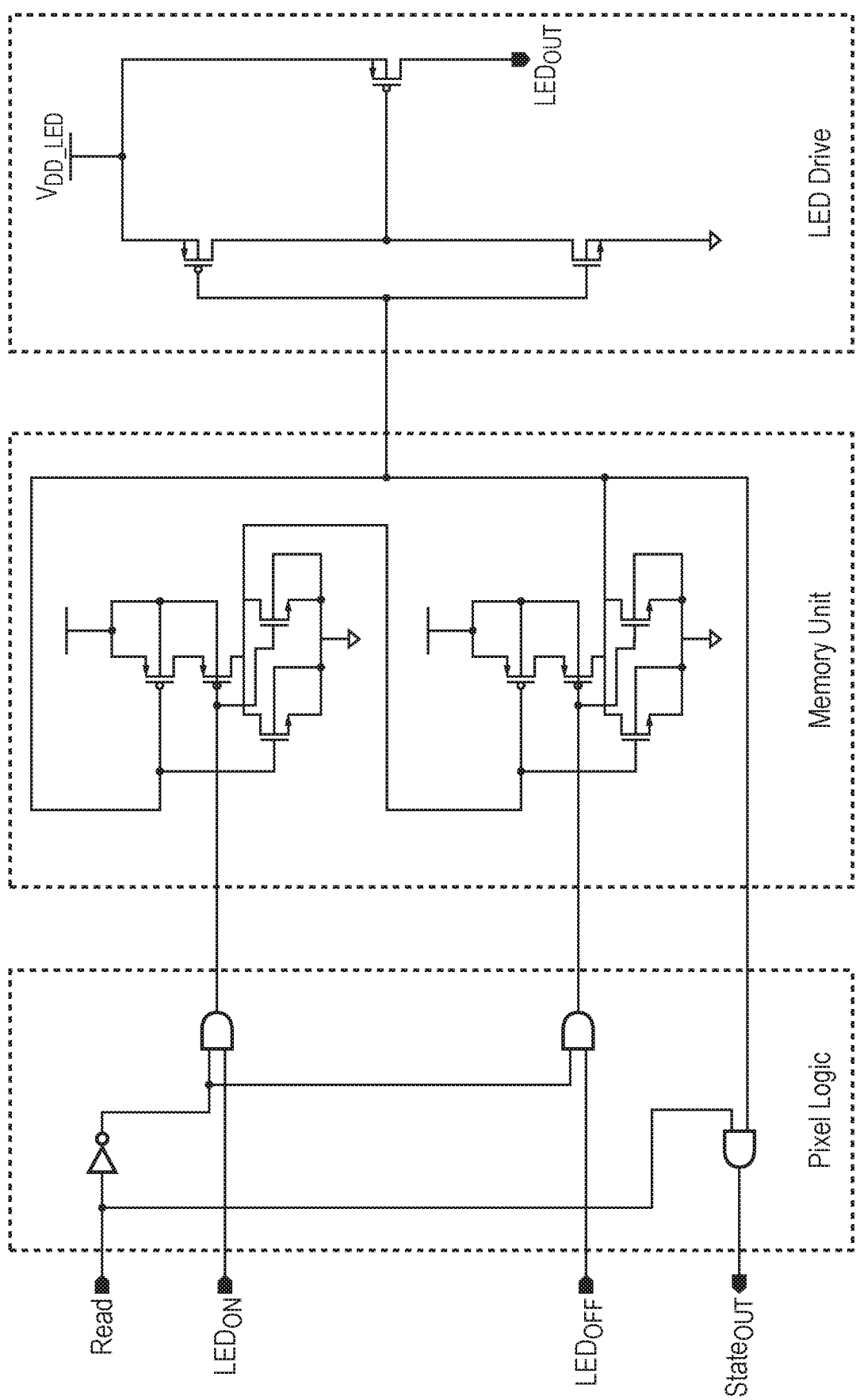
FIG. 7b is a more detailed diagram of the circuit.
Figure 8B:
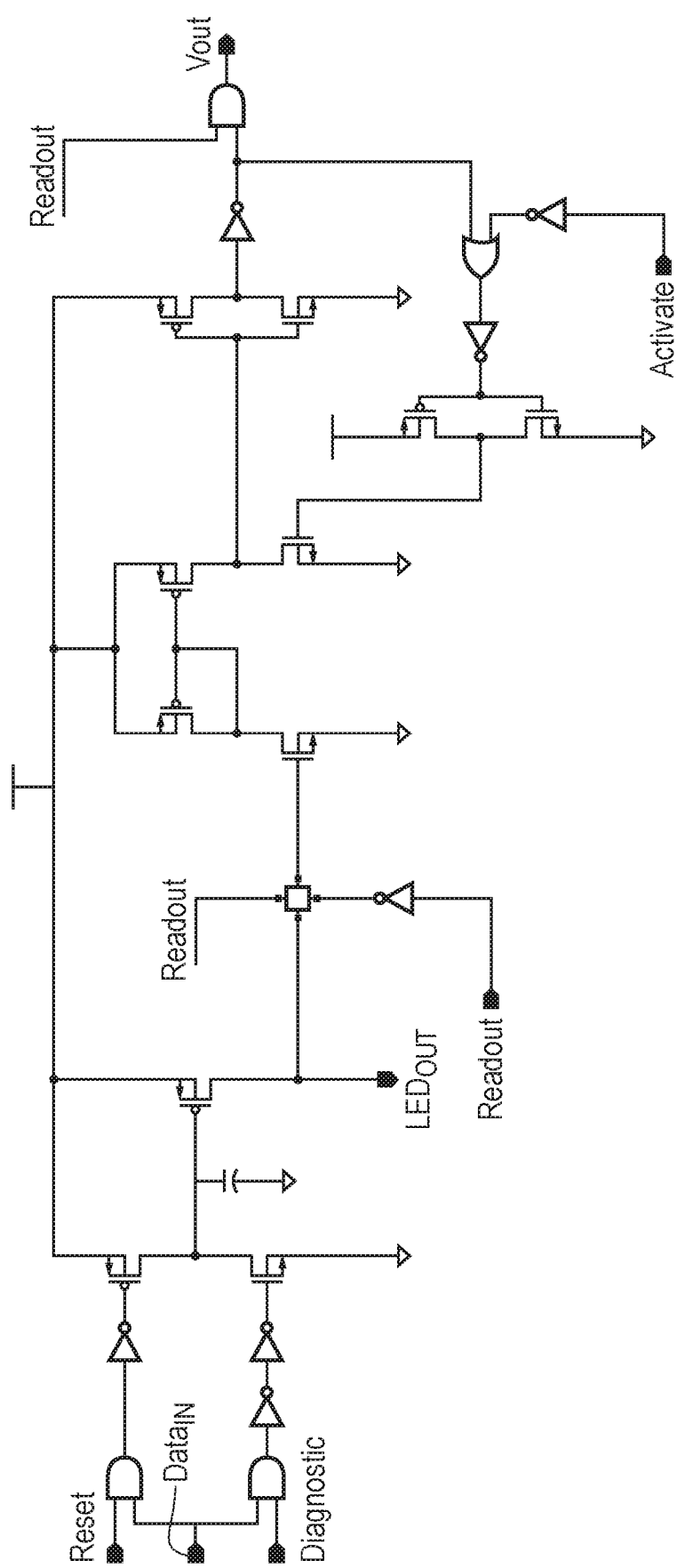
FIG. 8b is a more detailed diagram of the circuit.

FIGS. 6, 7 and 8 show control components of the optrode arrangement in schematic block diagram form (FIGS. 6a, 7a and 8a) and in slightly more detailed form (FIGS. 6b, 7b and 8b).

FIGS. 6a and 6b show a logic control circuit. This circuit dictates the operation mode (stimulation or diagnostic) of the optrode arrangement and dictates selection of the LED(s) to use. The communication protocol into the logic control block is based on an adapted SPI method. It consists of a clock, activate, and input and output data paths. The simplified diagram of this block is demonstrated in FIG. 6b. Digital counter, shift register and decoder are implemented respectively. The activate signal is a main control signal for optrode operation, which is based on global Clock signal and Data$_{IN}$ is utilized for serial data transmission to achieve addressing and controlling of LEDs. This enables selected LEDs to function in the selected operation mode.

Each LED control circuit comprises a stimulation control circuit and a diagnostic circuit, illustrated with simplified schematics in FIGS. 7 and 8 respectively.

The stimulation control circuit (see FIGS. 7a and 7b) consists of three elements: pixel logic, memory unit and LED drive. Stimulation operation is controlled by LED$_{ON}$, LED$_{OFF}$ and read signals. Pixel logic block receives external signals and transmits them to memory unit. Memory unit passes the control signals to the LED drive circuit, as well as saving the real-time state of LED (on/off) which can be transmitted back to the control unit via the readout port of the pixel logic block. Based on the control signals, the LED drive block connects or disconnects a drive current to the LED driven by analogue voltage source $V_{DD\_LED}$ to excite the LED to provide the required optical stimulation.

The diagnostic circuit schematically illustrated in FIGS. 8a and 8b drives the diagnostic operation mode of the optrode.

As noted above, the diagnostic mode can be conducted before stimulation operations or at any given time. This mode is used for abnormal condition detection. The normal working voltage of each LED is around 2.8V, but if an abnormal condition such as optrode breakage occurs then the voltage across any LED that is above the break or other abnormal point on the optrode will differ significantly from the normal working voltage (see FIG. 13). Thus, a measure of the voltage across a LED can be used to readily detect the presence of an abnormal condition. The proposed diagnostic circuit is based on this recognition that there will be a significant difference in voltage across an LED in an abnormal condition compared to a normal condition.

More specifically, under normal operation, the current through the LED will have a diode behaviour with applied $V_{DD\_LED}$ until limited by the control transistor. If however there is a significant abnormality such as an open circuit below the control transistor, this can be seen in the voltage at that point. This needs to be achieved whilst ensuring the voltage across the LED is below the turn-on voltage of 2.8V. The circuit layout can be seen in FIG. 8b.

The diagnostic circuit fundamentally consists of a pulse modulated DAC which determines the voltage across a diagnosing transistor. By imparting different voltage across the diagnostic transistor, different currents will be passed to the LED, leading to changes in $V_{LED}$. As such a voltage scan can be achieved and a profile built up of the target LED. As long as the connection is normal, it would be expected that increasing $V_{SG}$ across the control transistor will initially have a diode-like behaviour followed by saturation. If there is significant resistance e.g. contact corrosion between CMOS and LED then the diode like behaviour would become more resistive. Alternatively, if there is an open circuit formed due to probe breakage or otherwise, then $V_{LED}$ will stay significantly above of the normal saturation voltage.

In order to achieve this target, in this example four sampling points of $V_{IN}$ are set as 3.5V, 3.75V, 4.0V and 4.25V accordingly.

Digital-to-analogue conversion (DAC) is required for $V_{IN}$ sampling. Digital conversion is achieved via a simplified 1-bit sigma-delta converter. For different values of $V_{LED}$, the interval between output pulses will relate to the voltage. To achieve this an accurate counter is required downstream.

Figure 9:
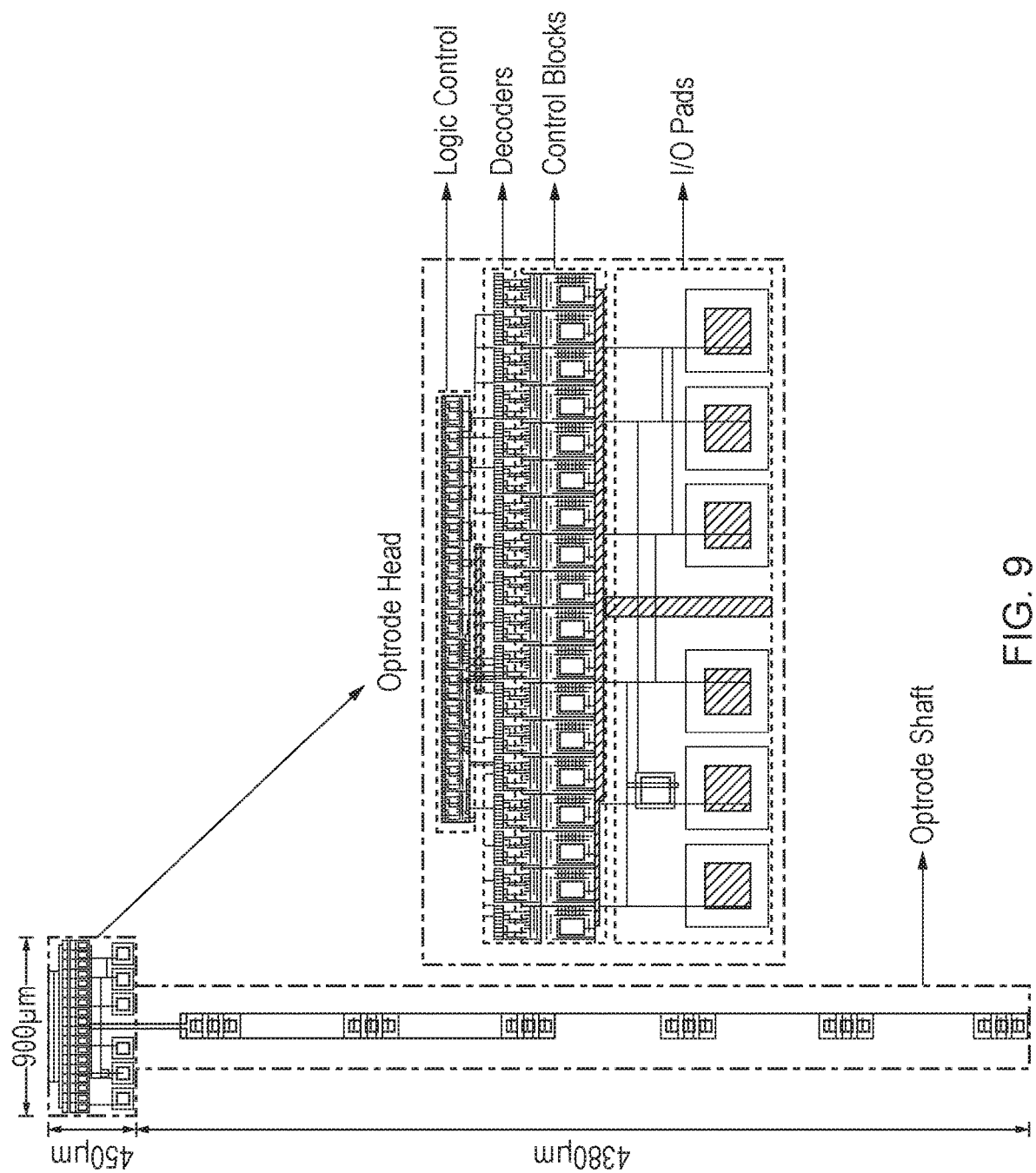
FIG. 9 is a schematic of the chip layout for the optrode head of the optrode of FIG. 4.

Turning to FIG. 9, an exemplary chip layout design is shown schematically. This example uses a 0.35-µm, 2-poly, 4-metal standard CMOS process for fabrication. The CMOS chip area is 900 µm×4830 µm, which is suitable for the proposed architecture in FIG. 2. The layout dimension of the optrode head is 900 µm×450 µm and 100 µm width is reserved for protection during the fabrication process. The size of LED control block is 50 µm×96 µm and the optrode shaft is 4380 µm×200 µm, which conforms to the system architecture.

Figure 10:
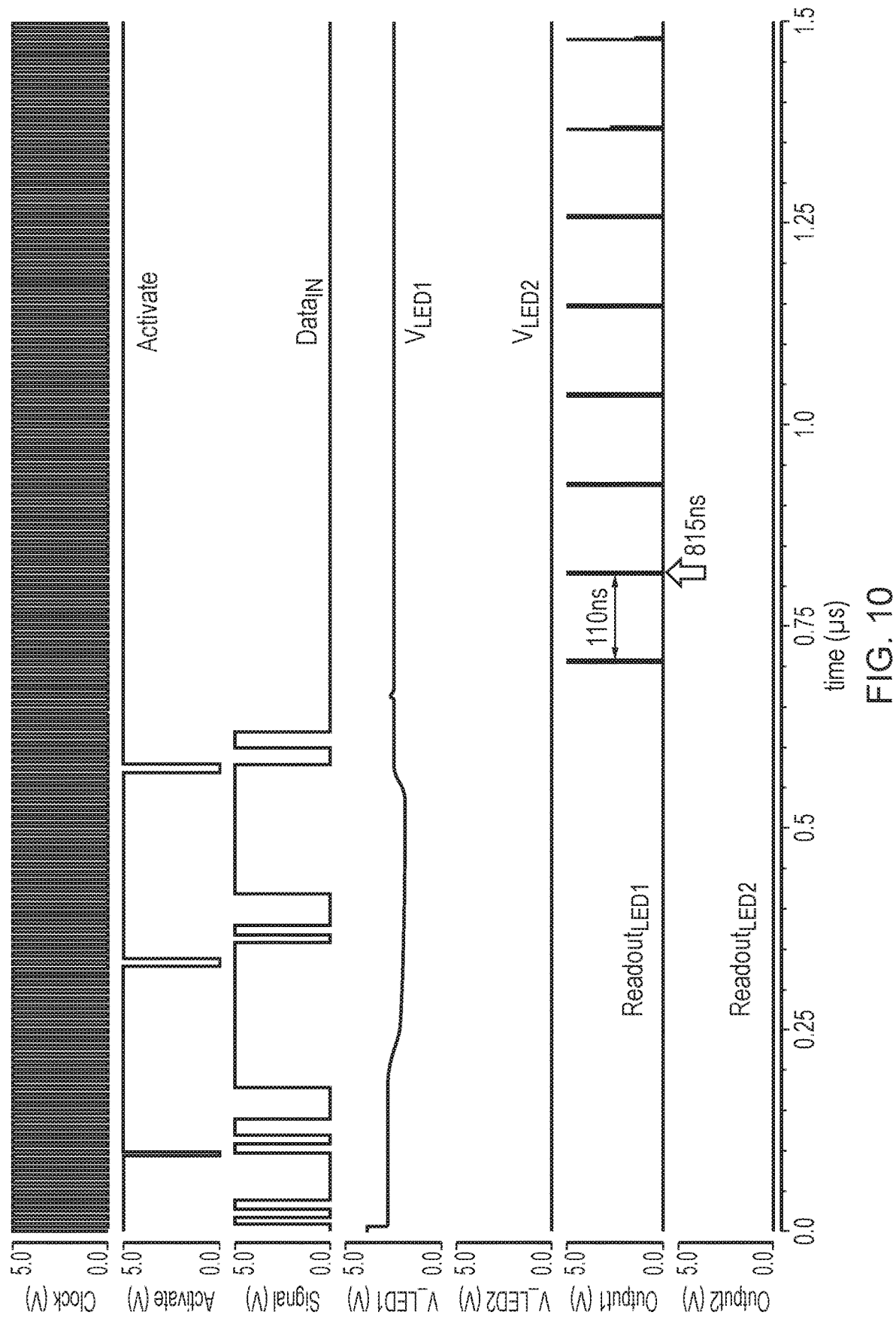
FIG. 10 schematically shows a simulation of the operation of an optrode in a diagnostic mode.

In order to validate the intended operation of the optrode assembly, a 'whole chip simulation' of the optrode design has been conducted. The diagnostic function was verified in the first instance and a schematic simulation result is illustrated in FIG. 10. In this simulation, two LEDs are randomly chosen for comparison, and one (LED$_1$) is operated in the diagnostic mode and another one (LED$_2$) is kept switched off. VIN is set as 3.75V for simulation purposes, with a corresponding input pulse width equal to 150 ns. Looking at FIG. 10, it can be seen that the diagnostic mode is triggered by the Activate signal, which is a control signal based on the Clock signal. The DataIN is used for logic control, addressing and input pulse width setting. On the output side, VLED$_1$ fluctuates during the PWM process and then remains static at 2.42V. In contrast, VLED$_2$ remains equal to zero throughout. The resultant signal form of ReadoutLED$_1$ is also clearly demonstrated by this simulation: the first recorded time interval of ReadoutLED$_1$ is obtained at 815 ns and the subsequent intervals are 110 ns. For ReadoutLED$_2$, as expected, there is no signal.

Using this simulation, for any given VIN, the respective VLED and time interval of readout pulse ($t_{interval}$) can be determined. Consequently, the relationship between VLED and $ti_{nternal}$ can be readily obtained as illustrated in FIG. 9. As expected, there is a negative correlation between these values when VLED has a value from 0.75V to 5V. When VLED is less than 0.75V, the $t_{interval}$ cannot be recorded due to the negligible current through the LED. Notably, an abnormal condition of an LED can be predictably recognised by the existence of an irregular $t_{interval}$.

Figure 13:
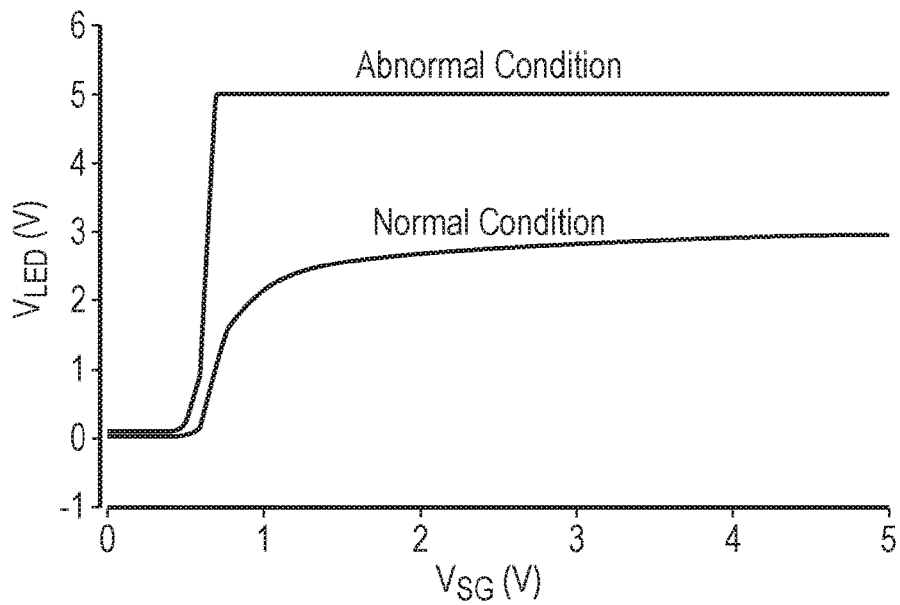
FIG. 13 is a graph showing a comparison simulation between normal and abnormal conditions.

It can be seen from FIG. 13 that for any given input voltage Vin there is a relevant output voltage V_LED. Furthermore, when Vin (Vsg) increases from 0V to 4.25V, VLED of normal condition decreases correspondingly while V_LED of abnormal condition keeps 5V constantly. Thus for diagnosis purpose, specific sampling points of Vin can be defined, and if related output results is recorded, then working condition of LED will be monitored and breakage point will be accordingly detected.

Figure 12:
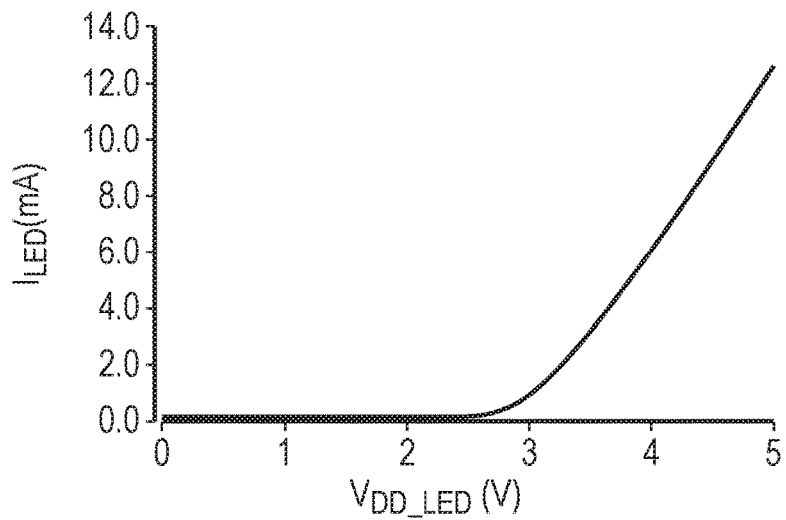
FIG. 12 is a graph showing current through LED versus drive voltage of LED obtained from a simulation of a stimulation mode of the optrode.

The simulation has also been used to prove the stimulation function of the proposed optrode. When the optrode is operated in stimulation mode, a specific LED is driven by VDD_LED with high current to achieve local light delivery. In this simulation, a sweeping of $V_{DD\_LED}$ is carried out in the simulation and the corresponding current through the LED ($I_{LED}$) is determined. The correlation curve between $V_{DD\_LED}$ and $I_{LED}$ is shown in FIG. 12 and it can be clearly seen that there is no measurable $I_{LED}$ when $V_{DD\_LED}$ is less than an LED working threshold. However, when $V_{DD\_LED}$ is greater than 2.8V, the LED is triggered and there is then an approximate linear relationship between $V_{DD\_LED}$ and $I_{LED}$.

A technical summary for the exemplary optrode is given in Table I.

TABLE I

PERFORMANCE SUMMARY

| | |
|---|---|
| Technology | 0.35-μm, 2-poly, 4-metal X-Fab CMOS process |
| Operation voltage | 5 V |
| Die Area | 4.38 mm2 |
| Optrode head size | 450 μm × 1000 μm |
| Optrode shraft size | 4380 μm × 200 μm |
| Stimulation sites quantity | 6 |
| LED quantity | 18 |
| LED control block size | 50 μm × 96 μm |

FIG. 14 shows a plot of reverse current vs. LED temperature for an LED used in the exemplary optrode. It can be seen that there is a generally linear relationship between temperature and reverse current for a given reverse bias on the LED (in the case 2V). This relationship can be leveraged to use the LED itself as a temperature sensor.

Based on a lab experiment for an example LED, it can be seen from FIG. 14 that when LED temperature increases from 28° C. to 60° C., with a constant reverse biased voltage of 2V, the reverse current through LED increases from 52 nA to 84 nA linearly. This reverse current can be converted into a corresponding voltage to be read out. In this way, the proposed sensor could detect a rise in LED temperature by measuring the LED reverse current.

FIG. 15 shows the reverse current converted into a corresponding voltage, through an appropriate current conveyor and a transimpedance amplifier (TIA) to give a linear relationship between the output voltage (of the LED temperature sensor circuit) and LED temperature. Thus it is possible to monitor LED temperature in real-time by reading out the output voltage of the LED temperature sensor circuit.

FIG. 16 shows a diagram of an example control circuit for using the LED as a temperature sensor. The circuit utilises a T-gate (TG) and an analogue multiplexer (MUX) to achieve a two-function configuration both for stimulation mode and temperature sensing. Wth TG open and the MUX set to connect the LED cathode to the ground (GND) terminal, the LED operates in stimulation mode. On the other hand, by switching off TG and at the same time setting the MUX to connect the LED cathode to reverse biased voltage $V_{reverse}$ (e.g. 2V), the LED can be used in a diagnostic mode in which it is possible to perform an LED-based temperature sensing function.

FIG. 17 shows a plot of $V_{out}$ vs. humidity for a capacitor-based humidity sensor, which it is proposed could be used as a humidity sensor for the optrode. For example, the capacitor of a humidity sensor could be incorporated in a CMOS implementation of the optrode by using two top metal layers in a standard CMOS process as two parallel plates of the capacitor. Since moisture has a correlation with capacitance, if the humidity changes, then the capacitance will be changed correspondingly. On this basis, the capacitor can be used as a humidity sensor. By incorporating an appropriate charging/discharging circuit, the change of capacitance resulting from a change in humidity could be converted into a change of voltage to be readout. This enables the humidity to be monitored by proposed sensor.

Figure 18:
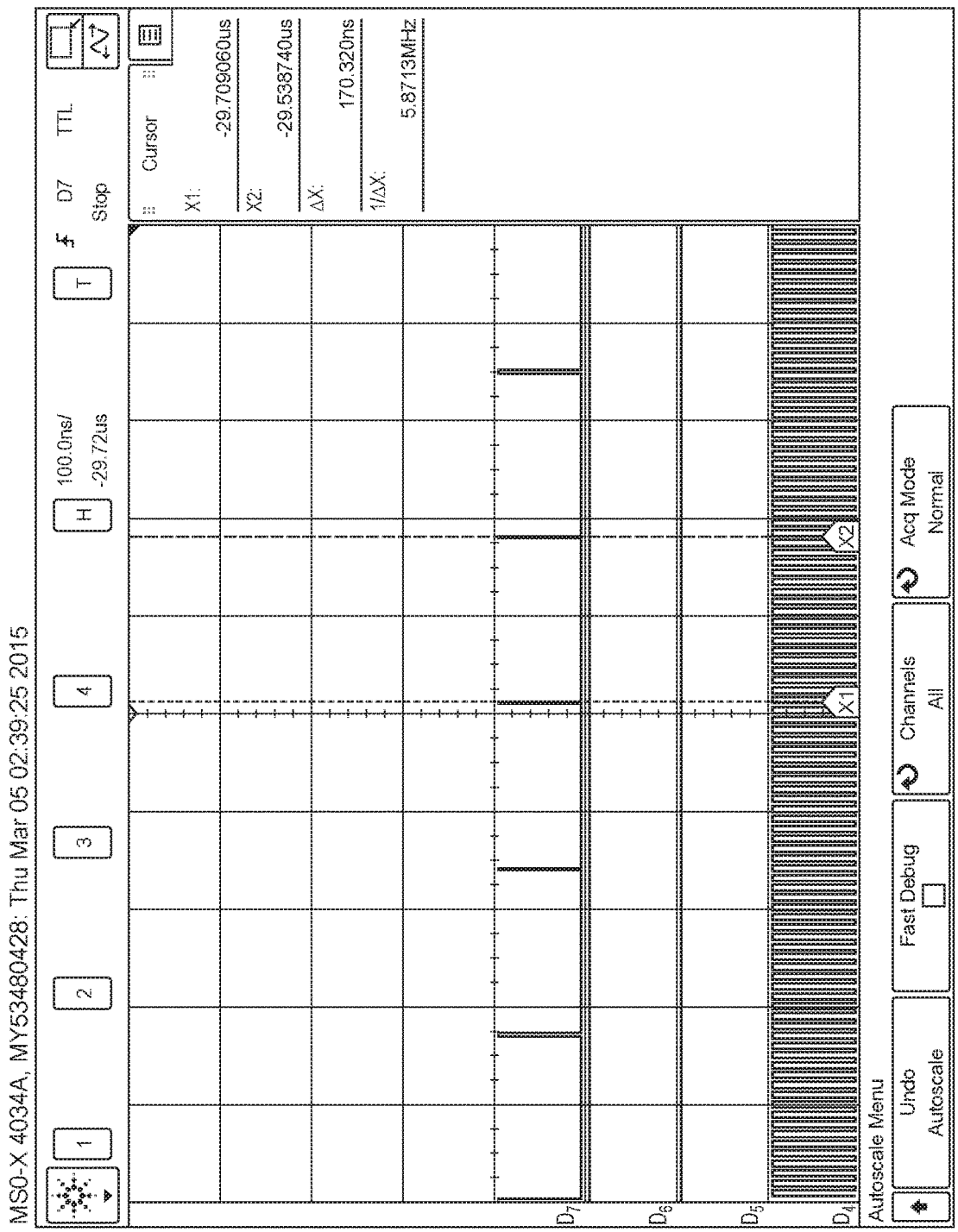
FIG. 18 shows an output from the optrode operating in diagnostic mode when the optrode is operating in a "normal" state.
Figure 19:
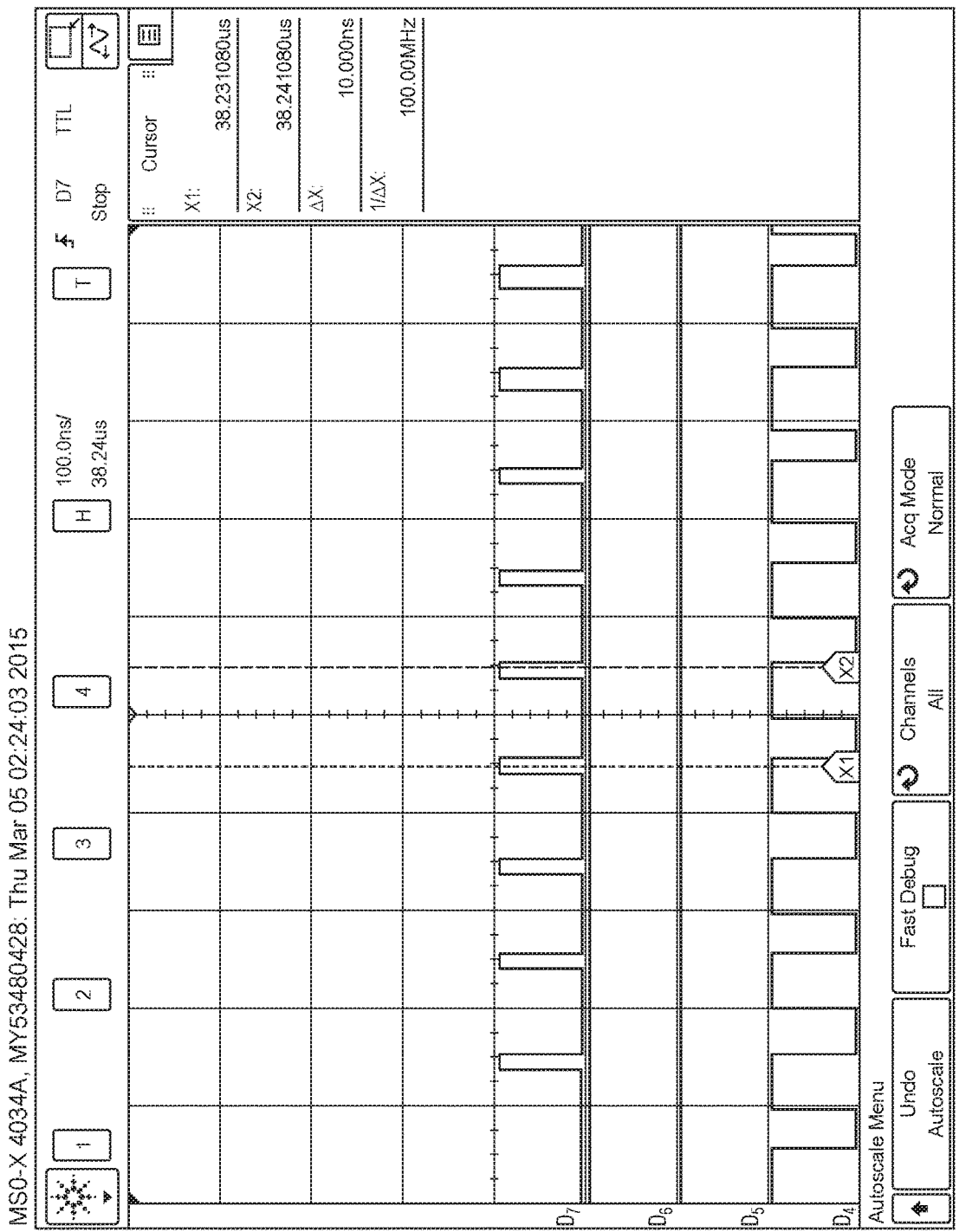
FIG. 19 shows an output from the optrode operating in diagnostic mode when the optrode is in an "abnormal" state.

FIGS. 18 and 19 illustrate how LED voltage can be used in the optrode's diagnostic mode to determine an "abnormal" versus a "normal" state of operation.

A "normal" state of operation is considered to mean the function of the optrode is good; the LED is operating as expected. In this normal operating state the current through the LED will have a diode behaviour with applied VDD_LED until limited by the control transistor.

An "abnormal" state of operation suggests is a state in which the operation is not "normal" and will suggest there is a problem with the optrode and/or LED. Possible problems that would result in an "abnormal" state of operation include: 1) increased resistance, for example due to corrosion (e.g. contact corrosion between LED and CMOS); 2) open circuit, for example as result of probe breakage or LED contact burnout; and 3) short circuit to tissue, for example as a result of probe fracture or LED failure).

The diagnostic circuit fundamentally consists of a pulse modulated DAC which determines the voltage on the diagnosing transistor Mdiag which acts as a current drive to the LED. The diagnostic drive currents vary quadratically allowing a large dynamic range, and cause a subsequent voltage across the LED, which can be read as $V_{LED}$ by the amplifier. As such a voltage scan can be achieved and a profile built up of the target LED. If there is a significant abnormality such as an open circuit south of the control transistor, this can be seen in the voltage at that point. For example, if there is significant resistance e.g. contact corrosion between CMOS and LED then the diode like behaviour would become more resistive. Alternatively, if there is an open circuit formed due to probe breakage or otherwise, the $V_{LED}$ will stay significantly above the normal saturation voltage.

The pulse modulated DAC is used for $V_{IN}$ generation. Digital conversion is achieved via a simplified 1-bit sigma-delta converter. For different values of $V_{LED}$, the interval between output pulses will relate to the voltage.

Figure 11:
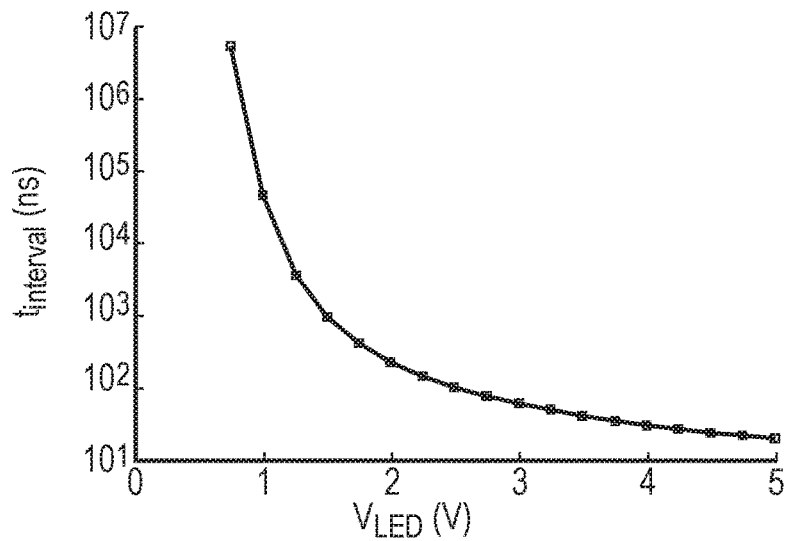
FIG. 11 is a graph showing the interval of output pulse versus voltage across LED obtained using the simulation illustrated by FIG. 8.

More specifically, and with reference to the oscilloscope outputs seen in FIGS. 18 and 19, in the diagnostic circuit, $V_{IN}$ is modulated by the pulse width of $Data_{IN}$ post header. The accuracy of $V_{IN}$ modulation is therefore determined by the pulse width modulation accuracy. Similarly the resultant $V_{LED}$ voltage is converted to a pulse frequency with interval $t_{interval}$. This can be seen in FIG. 11.

In a diagnostic mode, the intention is that the LED is not switched on. Consequently, in the normal condition $V_{LED}$ should be smaller than 2.5V (using the example LEDs described here). Then for normal condition, it can be seen from FIG. 11 that the output $t_{interval}$ should not be smaller than 100 ns. In lab experiment measurements for the example optrode the output $t_{interval}$ was observed using an oscilloscope. It can be seen from FIG. 18 that when the optrode works under normal condition with a specific $V_{IN}$, the $t_{interval}$ is 170 ns which matches expected results based on a simulation. Thus, the functionality of the diagnostic circuit has been verified when optrode is operating under normal condition.

In abnormal condition, however, $V_{LED}$ will differ from the normal condition. In one example, shown in FIG. 13, $V_{LED}$ is or has increased to 5V. Thus for abnormal condition, it can be seen from FIG. 11 that the output $t_{interval}$ should be very small, around 10 ns. Again, lab experiment measurements for the example optrode were conducted and the output $t_{interval}$ observed by oscilloscope. It can be seen from FIG. 19 that when optrode works under abnormal condition with specific $V_{IN}$, the $t_{interval}$ is 10 ns which also matches expected results based on a simulation. Thus, the functionality of the diagnostic circuit has been verified when the optrode is under an example abnormal condition.

Thus, in the above way, it is possible to operate the optrode in a diagnostic mode to the LED working condition in real-time and accurately diagnose an abnormality of the LED or optrode.

Various variations and modifications to the specifically described example are possible within the scope of the invention. For example, whereas in the described example a voltage measurement across each LED is used to determine the condition of the LEDs and the integrity of the optrode itself, alternative sensors may be used to determine the integrity of the optrode and/or for determining other operational parameters of the optrode system useful in diagnosis of potential faults in the system.

REFERENCES

[1] S. F. Cogan, "Neural Stimulation and Recording Electrodes," *Annual Review of Biomedical Engineering*, vol. 10, pp. 275-309, 2008.
[2] G. Nagel, T. Szellas, W. Huhn, S. Kateriya, N. Adeishvili, P. Berthold, et al., "Channelrhodopsin-2, a directly light-gated cation-selective membrane channel," *Proceedings of the National Academy of Sciences*, vol. 100, pp. 13940-13945, Nov. 25, 2003.
[3] V. Poher, N. Grossman, G. T. Kennedy, K. Nikolic, H. X. Zhang, Z. Gong, E. M. Drakakis, E. Gu, M. D. Dawson, P. M. W. French, P. Degenaar, and M. A. A. Neil, "Micro-LED arrays: A tool for two-dimensional neuron stimulation," *J. Phys. D-Appl. Phys.*, vol. 41, no. 9, p. 9, 2008, 094014.
[4] L. Golan, I. Reutsky, N. Farah, and S. Shoham, "Design and characteristics of holographic neural photo-stimulation systems," *J. Neural. Eng.*, vol. 6, p. 14, 2009, 66004.
[5] Farah, N.; Reutsky, I.; Shoham, S., "Patterned Optical Activation of Retinal Ganglion Cells," *Engineering in Medicine and Biology Society, 2007. EMBS 2007. 29th Annual International Conference of the IEEE*, pp. 6368, 6370, 22-26 Aug. 2007.
[6] Grossman, N.; Nikolic, K.; Toumazou, C.; Degenaar, P., "Modeling Study of the Light Stimulation of a Neuron Cell With Channelrhodopsin-2 Mutants," *Biomedical Engineering, IEEE Transactions on*, vol. 58, no. 6, pp. 1742, 1751, June 2011.
[7] P. Degenaar, N. Grossman, M. A. Memon, J. Burrone, M. Dawson, E. Drakakis, M. Neil, and K. Nikolic, "Optobionic vision—A new geneti-cally enhanced light on retinal prosthesis," *J. Neural Eng.*, vol. 6, 2009.
[8] W. J. Alilain, X. Li, K. P. Horn, R. Dhingra, T. E. Dick, S. Herlitze, et al., "Light-Induced Rescue of Breathing after Spinal Cord Injury," The Journal of Neuroscience, vol. 28, pp. 11862-11870, Nov. 12, 2008.
[9] McGovern, B., Berlinguer Palmini, R., Grossman, N., Drakakis, E., Poher, V., Neil, M. A. A., Degenaar, P., "A New Individually Addressable Micro-LED Array for Photogenetic Neural Stimulation," Biomedical Circuits and Systems, IEEE Transactions on, vol. 4, no. 6, pp. 469, 476, December 2010

The invention claimed is:

1. An optrode arrangement for delivering optical stimulation to target tissue in a patient, the optrode arrangement comprising:
    an implantable optrode comprising at least one electrically powered light emitter;
    an electrical circuit and control lines for controlling the light emitter; and
    a controller having two modes of operation, a stimulation mode in which the controller controls the light emitter to deliver optical stimulation to the target tissue and a diagnostic mode in which the controller determines a condition of one or both of the light emitter and/or the optrode;
    wherein the optrode arrangement is configured such that a voltage above a threshold voltage must be applied to an input of the light emitter to cause it to emit light for optical stimulation and wherein during operation of the controller in the diagnostic mode a non-zero voltage applied to the input of the light emitter does not exceed said threshold voltage.

2. An optrode arrangement according to claim 1, wherein the controller is configured to determine the condition of the light emitter to be normal or abnormal.

3. An optrode arrangement according to claim 2, wherein the controller is configured to generate an alert in the case that it is determined that the condition of the light emitter is abnormal.

4. An optrode arrangement according to claim 2, wherein the controller is configured, when it is determined that the condition of the light emitter is abnormal, to prevent subsequent operation in the stimulation mode.

5. An optrode arrangement according to claim 1, wherein in the diagnostic mode of operation, the controller determines a condition of the light emitter based on at least a voltage drop across the light emitter.

6. An optrode arrangement according to claim 5, wherein the controller comprises a diagnostic circuit configured to output a measure of voltage drop across the light emitter.

7. An optrode arrangement according to claim 6, wherein the controller is configured to compare the output of said diagnostic circuit with an expected output for a normal condition of the light emitter and to determine that the light emitter has an abnormal condition when the output of the diagnostic circuit is different from the expected output.

8. An optrode arrangement according to claim 1, comprising a thermal sensor for measuring a temperature of the optrode, wherein in the diagnostic mode of operation, the controller determines a condition of the light emitter based on at least an output from the thermal sensor.

9. An optrode arrangement according to claim 1, wherein the optrode comprises a plurality of stimulation sites space apart along the optrode from one another, each stimulation site comprising at least one light emitter.

10. An optrode arrangement according to claim 9, wherein each stimulation site comprises at least two light emitters.

11. An optrode arrangement according to claim 1, wherein the or each light emitter is a light emitting diode.

12. An optrode arrangement according to claim 1, wherein the target tissue is nerve cells.

13. An optrode arrangement for delivering optical stimulation to target tissue in a patient, the optrode arrangement comprising:
   an implantable optrode comprising at least one electrically powered light emitter;
   an electrical circuit and control lines for controlling the light emitter; and
   a controller having two modes of operation, a stimulation mode in which the controller controls the light emitter to deliver optical stimulation to the target tissue and a diagnostic mode in which the controller determines a condition of one or both of the light emitter and/or the optrode;
   wherein the optrode arrangement is configured such that a voltage above a threshold voltage must be applied to an input of the light emitter to cause it to emit light for optical stimulation and wherein during operation of the controller in the diagnostic mode a non-zero voltage applied to the input of the light emitter does not exceed said threshold voltage,
   wherein in the diagnostic mode of operation, the controller determines a condition of the light emitter based on at least a voltage drop across the light emitter.

14. An optrode arrangement according to claim 11, wherein the controller comprises a diagnostic circuit configured to output a measure of voltage drop across the light emitter.

15. An optrode arrangement according to claim 11, wherein the controller is configured to compare the output of said diagnostic circuit with an expected output for a normal condition of the light emitter and to determine that the light emitter has an abnormal condition when the output of the diagnostic circuit is different from the expected output.

16. An optrode arrangement according to claim 11, wherein the controller is configured to determine the condition of the light emitter to be normal or abnormal.

17. An optrode arrangement according to claim 16, wherein the controller is configured to generate an alert in the case that it is determined that the condition of the light emitter is abnormal.

18. An optrode arrangement according to claim 16, wherein the controller is configured, when it is determined that the condition of the light emitter is abnormal, to prevent subsequent operation in the stimulation mode.

19. An optrode arrangement according to claim 11, wherein the optrode comprises a plurality of stimulation sites space apart along the optrode from one another, each stimulation site comprising at least one light emitter.

20. An optrode arrangement for delivering optical stimulation to target tissue in a patient, the optrode arrangement comprising:
   an implantable optrode comprising at least one electrically powered light emitter;
   an electrical circuit and control lines for controlling the light emitter; and
   a controller having two modes of operation, a stimulation mode in which the controller controls the light emitter to deliver optical stimulation to the target tissue and a diagnostic mode in which the controller determines a condition of one or both of the light emitter and/or the optrode;
   wherein the optrode arrangement is configured such that a voltage above a threshold voltage must be applied to an input of the light emitter to cause it to emit light for optical stimulation and wherein during operation of the controller in the diagnostic mode a non-zero voltage applied to the input of the light emitter does not exceed said threshold voltage, and
   a thermal sensor for measuring a temperature of the optrode, wherein in the diagnostic mode of operation, the controller determines a condition of the light emitter based on at least an output from the thermal sensor.

* * * * *

UNITED STATES PATENT AND TRADEMARK OFFICE
CERTIFICATE OF CORRECTION

PATENT NO. : 11,040,216 B2
APPLICATION NO. : 15/319721
DATED : June 22, 2021
INVENTOR(S) : Patrick Degenaar et al.

Page 1 of 1

It is certified that error appears in the above-identified patent and that said Letters Patent is hereby corrected as shown below:

In the Claims

Column 16, Claim 14, Line 1:
"according to claim 11," should read: -- according to claim 13, --.

Column 16, Claim 15, Line 5:
"according to claim 11," should read: -- according to claim 13, --.

Column 16, Claim 16, Line 11:
"according to claim 11," should read: -- according to claim 13, --.

Column 16, Claim 19, Line 22:
"according to claim 11," should read: -- according to claim 13, --.

Signed and Sealed this
Twenty-sixth Day of July, 2022

Katherine Kelly Vidal
*Director of the United States Patent and Trademark Office*